United States Patent [19]
Nakanishi et al.

[11] Patent Number: 6,090,966
[45] Date of Patent: Jul. 18, 2000

[54] PREPARATION OF CONTRACT MASS FOR ALKYLHALOSILANE PRODUCTION AND PROCESS FOR PRODUCING ALKYLHALOSILANES

[75] Inventors: Tetsuo Nakanishi; Tetsuya Inukai, both of Usui-gun; Kazumasa Tsukioka, Annaka; Hiroshi Nakayama, Annaka; Yukinori Satoh, Annaka, all of Japan

[73] Assignee: Shin-Etsu Chemical Co., Ltd., Japan

[21] Appl. No.: 09/076,153

[22] Filed: May 12, 1998

[30] Foreign Application Priority Data

May 13, 1997 [JP] Japan ..................................... 9-137655

[51] Int. Cl.⁷ ......................................................... C07F 7/16
[52] U.S. Cl. ............................................ 556/472; 423/342
[58] Field of Search ............................... 556/472; 423/342

[56] References Cited

U.S. PATENT DOCUMENTS

| | | |
|---|---|---|
| 4,218,387 | 8/1980 | Mass et al. . |
| 4,500,724 | 2/1985 | Ward, III et al. . |
| 4,864,044 | 9/1989 | Lewis et al. . |
| 4,895,969 | 1/1990 | Feldner et al. ........................... 556/472 |
| 5,015,751 | 5/1991 | Feldner et al. ........................... 556/472 |
| 5,712,405 | 1/1998 | Nakayama et al. ...................... 556/472 |

FOREIGN PATENT DOCUMENTS

| | | |
|---|---|---|
| 256 876 | 2/1988 | European Pat. Off. . |
| 372 341 | 6/1990 | European Pat. Off. . |
| 372 918 | 6/1990 | European Pat. Off. . |
| 440 414 | 8/1991 | European Pat. Off. . |

OTHER PUBLICATIONS

Astract—CA 1246533.

*Primary Examiner*—James O. Wilson
*Assistant Examiner*—Howard Owens
*Attorney, Agent, or Firm*—Millen, White, Zelane & Branigan, P.C.

[57] ABSTRACT

Alkylhalosilanes are produced by first fluidizing a metallic silicon powder with an inert gas, preheating the silicon powder at a temperature between 200° C. and a steady reaction temperature while keeping the silicon powder fluidized, adding a copper catalyst to the preheated silicon powder to form a contact mass, and feeding an alkyl halide into the contact mass whereby the alkylhalosilanes are formed by direct synthesis. This process prevents the copper catalyst from being sintered by thermal hysteresis and activates a high catalysis on the contact mass at the start of reaction. The desired dialkyldihalosilane can be produced at a high selectivity.

17 Claims, 1 Drawing Sheet

PREPARATION OF CONTRACT MASS FOR ALKYLHALOSILANE PRODUCTION AND PROCESS FOR PRODUCING ALKYLHALOSILANES

BACKGROUND OF THE INVENTION

1. Field of the Invention

This invention relates to a method for preparing a contact mass for use in the production of alkylhalosilanes by the direct process and a process for producing alkylhalosilanes using the contact mass. More particularly, it relates to a process for continuously producing alkylhalosilanes by effecting gas-solid contact reaction between metallic silicon powder and an alkyl halide in the presence of a copper catalyst.

2. Prior Art

With respect to the synthesis of alkylhalosilanes, Rochow first disclosed in U.S. Pat. No. 2,380,995 direct synthesis reaction between metallic silicon and alkyl halides in the presence of copper catalysts. Since then, there have been reported a number of research works relating to various co-catalysts used together with copper catalysts, various copper catalysts and treatment thereof, reactors, additives used during reaction, and the like.

The direct synthesis process involves activating a contact mass comprising metallic silicon and a copper catalyst and introducing an alkyl halide into the activated contact mass for accomplishing direct gas-solid contact between metallic silicon and alkyl halide, thereby producing alkylhalosilanes. The period required to activate the contact mass is defined by R. J. H. Voorhoeve, Organohalosilanes, 1967, pp. 250–251, as a time taken until a phase of $Cu_3Si$ active in direct synthetic reaction (η phase) is formed in the contact mass. This is generally known as an "induction period." Various methods have been proposed for reducing the induction period.

JP-B 43400/1988, for example, discloses an alkylhalosilane producing method involving charging a reactor with silicon, catalyst and co-catalyst, passing nitrogen through the reactor, heating the reactor up to 200° C., admitting methyl chloride, heating the reactor up to 345° C., maintaining the temperature for 1 hour, and thereafter, cooling the reactor to 330° C. This method allows a larger amount of methyl chloride to be admitted. It is described that the reaction mass should be treated above 340° C. for about 20 to 30 minutes when reaction is done at a temperature below 340° C., and that such treatment is unnecessary when reaction is done at a temperature above 340° C. or when copper chloride is used.

JP-A 78390/1979 discloses the steps of commencing reaction at 360° C. in order to reduce the induction period, lowering the temperature by 10° C. in each of initial 2-hour periods and thereafter, lowering the temperature at a rate of 15° C./hr. until 280° C. is reached.

According to these methods, the contact mass is once heated to a temperature above the steady reaction temperature, and the temperature is then lowered for reaction to continue. Once heated to the elevated temperature, however, the copper catalyst is spent and likely to lower its catalytic activity at lower temperatures. It is also known that copper and similar solid catalysts become sintered owing to the thermal hysteresis at elevated temperatures. With the progress of sintering, the catalyst life becomes shorter and the yield of the desired dialkyldihalosilane becomes lower.

The procedure of once heating to a higher temperature and then cooling to the steady reaction temperature is undesirable from the energy standpoint partly because the reaction of alkyl halide with metallic silicon is exothermic. This is disadvantageous especially in the case of commercial scale reactors. Additionally, the cooling step takes a long time. If a long time is passed until the steady reaction temperature is reached, there is a likelihood of failure to activate to the catalyst.

JP-A 187933/1986 discloses another alkylhalosilane producing method involving passing nitrogen through a reactor charged with metallic silicon powder and a copper catalyst for fluidization, heating the reactor at 325° C., passing HCl gas for 75 minutes to produce trichlorosilane, thereafter charging the reactor with an accelerator, and feeding methyl chloride for reaction to continue. This method, however, uses HCl as one reactant, on account of which tetrachlorosilane and trichlorosilane form. These chlorosilanes are generally difficult to separate from other useful silanes.

Furthermore, JP-B 40035/1989 discloses pretreatment by heating a mixture of metallic silicon powder, catalyst, and co-catalyst to 300° C. and then introducing an equimolar mixture of dimethyldichlorosilane and methyl chloride. This method, however, is less effective to activate the catalyst. Even if the reaction is activated, the dialkyldihalosilane used in the pretreatment goes to waste.

In summary, prior art alkylhalosilane producing methods suffer from the following problems associated with the activation of the contact mass. (1) The copper catalyst can be sintered during long-term thermal hysteresis at elevated temperatures, resulting in the catalyst losing lifetime and selectivity. (2) Excessive heating is disadvantageous from the energy standpoint. (3) A longer induction period fails to activate. (4) Extra HCl is used with formation of by-products which are difficult to separate, leading to a lowering of selectivity.

SUMMARY OF THE INVENTION

Therefore, an object of the present invention is to provide a novel and improved method for preparing a contact mass for use in the production of alkylhalosilanes, the contact mass having a sufficient catalytic activity to ensure a long lifetime and a high selectivity during reaction.

Another object of the present invention is to provide a novel and improved process for producing alkylhalosilanes by direct synthesis using the contact mass so that the desired alkylhalosilane may be produced at a high selectivity over a long period of time.

Making investigations on the process for preparing alkylhalosilanes by commercially advantageous direct synthesis, especially the step of activating a catalyst on the contact mass so as to ensure a long life and high selectivity during reaction while eliminating the problems arising from the sintering of the catalyst by thermal hysteresis, we have found that the problems of the prior art step of activating a catalysis on the contact mass can be solved by charging a heater or reactor with a metallic silicon powder, fluidizing the silicon powder with an inert gas, preheating the silicon powder at a temperature between 200° C. and a steady reaction temperature while keeping the silicon powder fluidized, then adding a copper catalyst to the preheated, fluidized silicon powder to form a contact mass, and feeding an alkyl halide into the contact mass in the reactor, thereby effecting continuous gas-solid contact reaction between the alkyl halide and the contact mass to produce alkylhalosilanes.

More particularly, by previously fluidizing only the metallic silicon powder, the heat amount given within the heater or reactor can be uniformly distributed throughout the silicon powder for fully drying the silicon powder. This eliminates moisture which is one reaction inhibiting factor. The late addition of the copper catalyst avoids sintering of the catalyst by thermal hysteresis and enables thorough mixing of the metallic silicon powder and the copper catalyst powder.

In a first aspect, the invention provides a method for preparing a contact mass for use in the production of alkylhalosilanes. A metallic silicon powder is fluidized with an inert gas. The silicon powder is preheated at a temperature between 200° C. and a steady reaction temperature while the silicon powder is kept fluidized. A copper catalyst is added to the preheated silicon powder, forming the contact mass.

In a second aspect, the invention provides a method for producing alkylhalosilanes of the general formula:

$$R_nSiX_{4-n}$$

wherein R is a lower alkyl group having 1 to 4 carbon atoms, X is a halogen atom, and letter n is an integer of 0 to 3, the method comprising the steps of fluidizing a metallic silicon powder with an inert gas; preheating the silicon powder at a temperature between 200° C. and a steady reaction temperature while keeping the silicon powder fluidized; adding a copper catalyst to the preheated silicon powder to form a contact mass; and feeding a reactant gas containing an alkyl halide into the contact mass whereby the silanes are formed by direct synthesis.

BRIEF DESCRIPTION OF THE DRAWINGS

The only figure, FIG. 1 schematically illustrates one exemplary system for producing alkylhalosilanes according to the invention.

DETAILED DESCRIPTION OF THE INVENTION

Figure 1:
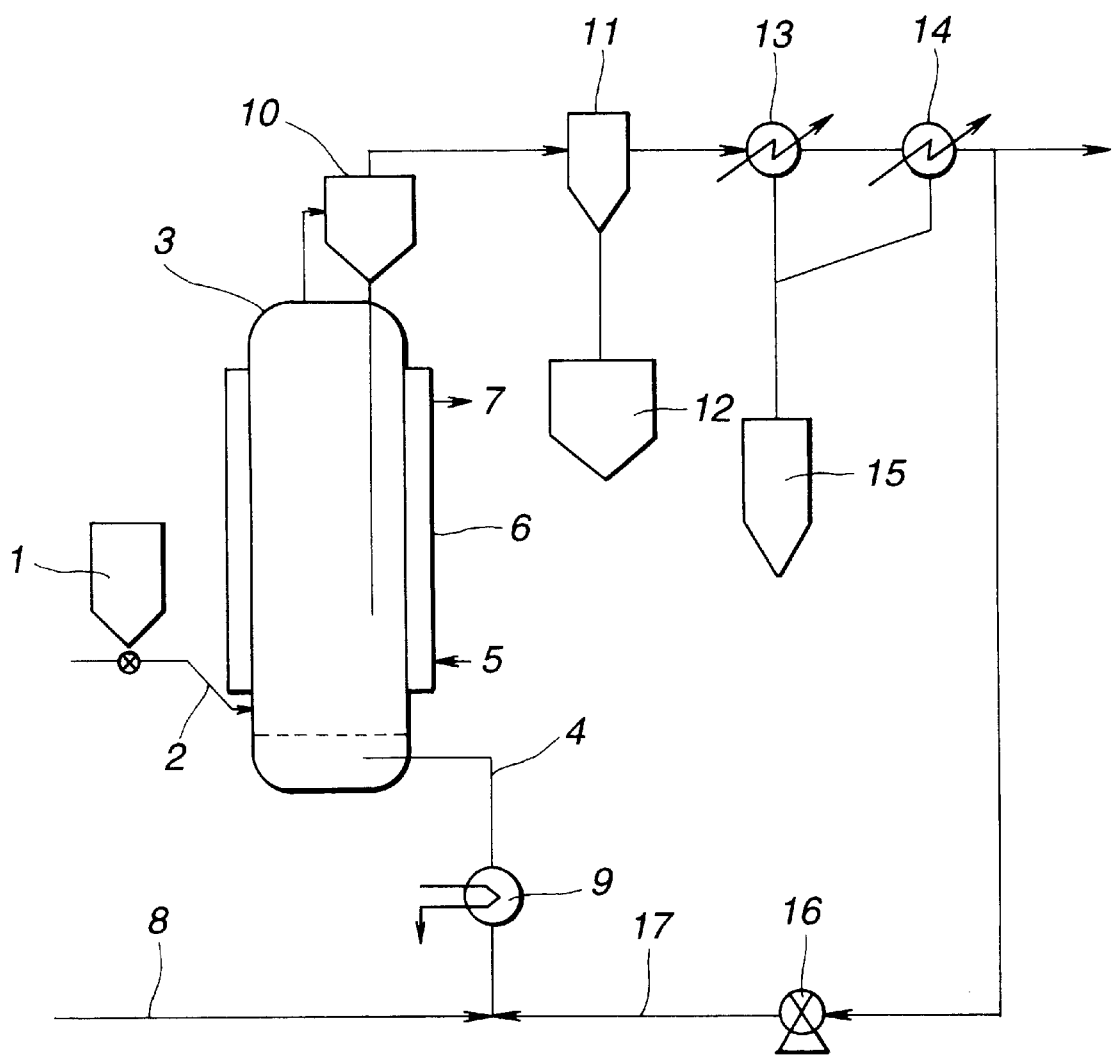

The invention pertains to a process for producing alkylhalosilanes. Broadly stated, alkylhalosilanes of the general formula:

$$R_nSiX_{4-n}$$

wherein R is an alkyl group having 1 to 4 carbon atoms, X is a halogen atom, and letter n is an integer of 0 to 3, are produced by introducing a reactant gas containing an alkyl halide into a contact mass comprising a metallic silicon powder and a copper catalyst whereby the alkylhalosilanes are formed by the direct synthesis process. According to the invention, while the metallic silicon powder is kept fluidized with an inert gas, the silicon powder is previously heated at a temperature of from 200° C. to a steady reaction temperature. Thereafter, the copper catalyst is added to the preheated, fluidized silicon powder to form the contact mass. The alkyl halide-containing reactant gas is introduced into this contact mass whereby the alkylhalosilanes are produced.

The metallic silicon used herein should preferably have a purity of at least 97% by weight, especially at least 98% by weight. Preferred is metallic silicon powder obtained by grinding metallic silicon to an appropriate particle size. Where the reactor used is a fluidized bed reactor or agitation reactor, metallic silicon powder having a particle size of 5 to 150 μm is preferred in order that the metallic silicon powder be appropriately fluidizing in the reactor. Note that the term "particle size" used herein is a particle size corresponding to 50% of a mass base cumulative oversize distribution curve by sieve analysis.

For the copper catalyst, any form of copper may be used, for example, elemental copper such as granular copper and stamped copper, copper alloys such as Cu—Si, and copper compounds such as cuprous oxide, cupric oxide, and copper chloride. The loading of the copper catalyst is preferably about 0.1 to 10 parts, especially about 2 to 8 parts by weight of copper per 100 parts by weight of the metallic silicon powder.

Together with the copper catalyst, promoters such as metallic zinc, antimony and tin powders may be used according to a well-known technique. The promoter may be used separately or as an alloy with copper, for example, Cu—Zn, Cu—Sn or Cu—Zn—Sn.

Alkyl halides are reacted with metallic silicon to form alkylhalosilanes. The alkyl halides used herein are those having 1 to 4 carbon atoms, for example, methyl chloride, ethyl chloride, propyl chloride, methyl bromide, and ethyl bromide. Among these, methyl chloride is commercially most useful. Dimethyldichlorosilane prepared using methyl chloride finds numerous applications as a raw material for a variety of silicone resins.

Desirably the alkyl halide reactant is previously heated and gasified before it is fed into the reactor. The alkyl halide gas may be used alone or in admixture with an inert gas. The feed amount of alkyl halide gas is calculated as an amount (combined with the inert gas) necessary to fluidize the contact mass and hence, properly determined from the diameter of a reactor used and a superficial velocity in a column.

According to the invention, the alkylhalosilanes are produced as follows. First, a metallic silicon powder is heated at 200° C. or higher while keeping the silicon powder fluidized with an inert gas. This heating may be carried out by means of a heater or by passing a hot heat carrier through a jacket around a reactor or an internal heat exchanger in a reactor. It is preferred to heat the metallic silicon powder at a higher temperature. If the temperature exceeds the reaction temperature, that is, the temperature for reaction of the metallic silicon powder with the alkyl halide to take place, there is a likelihood that the copper catalyst can be sintered or reduced in lifetime when it is charged later. For this reason, the preheating temperature should not exceed the steady reaction temperature.

The term "steady reaction temperature" designates the temperature of the contact mass in a continuous reactor during the period when reaction of the metallic silicon powder with the alkyl halide proceeds in a steady state, that is, the reaction period excluding the operation starting and ending stages. It is believed that in conventional direct synthesis processes, the steady reaction temperature is in the range of 250° C. to 350° C. In the practice of the invention, the steady reaction temperature is preferably regarded to range from 280° C. to 300° C. Therefore, in the contact mass preparation method of the invention, it is favorable that the temperature at which the metallic silicon powder is fluidized and heated is in the range of from 200° C. to 300° C., especially from 240° C. to 280° C. The metallic silicon powder is kept fluidized in this temperature range for about 1 to 15 hours, especially about 2 to 10 hours. The next step of adding the copper catalyst to the preheated silicon powder is preferably carried out in the above temperature range. In the step of activating a catalysis on the contact mass, the contact mass is advantageously kept at a temperature ±10° C. within the above temperature range for a certain time, preferably about 1 to 8 hours, more preferably about 2 to 5 hours because a catalytic activity ensuring a longer lifetime and a higher selectivity can be activated.

In the step of heating the metallic silicon powder or activating a catalysis, an inert gas is used for fluidizing the silicon powder or contact mass in the reactor. The inert gas used herein includes argon and nitrogen, with the nitrogen being preferred for economy. The flow velocity of inert gas may be at least the velocity at which the metallic silicon powder starts fluidizing, especially about 5 times the fluidization starting velocity. If the flow velocity of inert gas is below this range, uniform fluidization of the metallic silicon powder would be difficult. If the flow velocity of inert gas is beyond this range, more metallic silicon powder would scatter and the losses of inert gas and heat would increase. It is preferred to flow the inert gas in a circulating manner.

After the metallic silicon powder is preheated as above, the copper catalyst is admitted into the heater or reactor where it is mixed with the metallic silicon powder to form a contact mass. Where a promoter is used, it is added at the same time as the copper catalyst whereupon they are concurrently heated and mixed.

The foregoing steps may be carried out in a separate heater or directly in a reactor for alkylhalosilane production.

After the contact mass is given catalytic activity as mentioned above, the alkyl halide is introduced into the reactor whereby gas-solid contact reaction takes place between the alkyl halide and metallic silicon to form alkylhalosilanes. This reaction can be conventionally carried out.

The heater or reactor used in the alkylhalosilane producing process according to the invention may be any of well-known reactors including fluidized bed reactors and agitating fluidized bed reactors. For industrial manufacture, a fluidized bed reactor is used with the advantages of a high yield, a high selectivity, and effective utilization of energy. More desirably, the reactor is externally equipped with means (including a condenser, piping and a compressor) for circulating the unreacted alkyl halide gas and a cyclone or filter means for collecting scattered contact mass.

Referring to FIG. 1, there is illustrated an exemplary industrial scale system having a fluidized bed reactor incorporated for the production of alkylhalosilanes. When the alkylhalosilane is produced by this system, a metallic silicon powder is first fed from a silicon reservoir tank 1 to a fluidized bed reactor 3 through a source feed line 2, and an inert gas is introduced into the reactor 3 at its bottom through a gas feed line 4 for starting fluidization of the metallic silicon powder. A mixture of a small amount of metallic silicon powder and a cocatalyst may be fed. Then, a heat carrier is passed through a jacket 6 around the reactor 3 from an inlet 5 to an outlet 7 for heating the reactor 3 for thereby heating the metallic silicon powder at the preselected temperature. Thereafter, a catalyst mixture is fed from its source (not shown) into the reactor 3 through the source feed line 2 where the catalyst is mixed with the silicon powder to form a contact mass. After the contact mass is activated, an alkyl halide is fed from a reactant feed line 8 to a heater 9 where it is heated and then into the reactor 3 through the line 4. In the reactor, gas-solid contact reaction is effected between the alkyl halide and the contact mass to produce the alkylhalosilane. The system shown in FIG. 1 includes an output/circulating line from the reactor 3 including a cyclone 10 at the top of the reactor 3, another cyclone 11 for separating particles, a reservoir 12 for receiving the separated particles, condensers 13 and 14 for condensing silane gases, a reservoir 15 for receiving the condensed silanes, a compressor 16 for compressing the inert gas for circulation, and a return pipe 17 for feeding back the unreacted alkyl halide-carrying gas.

EXAMPLE

Examples of the invention are given below by way of illustration and not by way of limitation. All parts are by weight.

Example 1

A fluidized bed reactor of carbon steel having a diameter of 8 cm and a height of 1 m as shown in FIG. 1 was charged with 100 parts of a metallic silicon powder. While nitrogen gas was passed through the reactor at a flow velocity of 2 cm/sec for fluidizing the silicon powder, the reactor was heated to raise the interior temperature to 260° C. over 3½ hours. At the end of preheating, 4 parts of a catalyst mixture composed mainly of metallic copper and brass powders was admitted into the reactor.

Thereafter, the reactor interior temperature was gradually increased to 290° C. while methyl chloride was introduced into the reactor at a flow velocity of 7 cm/sec. The time taken until the temperature of 290° C. was reached was 2 hours. Reaction was continued at the interior temperature of 290° C. The reaction was terminated when the conversion of the metallic silicon powder exceeded 20% of the metallic silicon powder charge. Table 1 shows the running time from the start of methyl chloride introduction to the end of reaction.

Table 1 also shows STY as well as the proportions of monosilanes and high-boiling products relative to the entire methylchlorosilane product.

It is noted that the methylchlorosilane product contains dimethyldichlorosilane (D), methyltrichlorosilane (T), other methylchlorosilanes, and high-boiling products (R) having a boiling point above 80° C. under atmospheric pressure (e.g., disilanes). The amounts of these components are expressed by percents by weight based on the total weight of the methylchlorosilane product. The formation rate of methylchlorosilane is represented by a space time yield (STY) which is equal to the weight of methylchlorosilanes produced per unit time relative to the weight of metallic silicon held in the reactor, that is, {weight (g) of methylchlorosilanes}/{weight (kg) of metallic silicon}× (time (hr.)}.

Comparative Example 1

The same reactor as in Example 1 was charged with 100 parts of the metallic silicon powder and 4 parts of the catalyst mixture, both used in Example 1. While nitrogen gas was passed through the reactor for fluidizing the contact mass, the reactor was heated to raise the interior temperature to 260° C. over 3½ hours. Thereafter, methyl chloride was introduced into the reactor to initiate reaction while the reactor interior temperature was gradually increased to 290° C. The time taken until the temperature of 290° C. was reached was 2 hours. Reaction was continued at the interior temperature of 290° C. The reaction was terminated when the conversion of the metallic silicon powder exceeded 20% of the metallic silicon powder charge. The results are shown in Table 1.

Comparative Example 2

The same reactor as in Example 1 was charged with 100 parts of the metallic silicon powder. While nitrogen gas was passed through the reactor for fluidizing the silicon powder, the reactor was heated to raise the interior temperature to 180° C. over 1 hour. Then 4 parts of the catalyst mixture used in Example 1 was admitted into the reactor.

After 2 hours, methyl chloride was introduced into the reactor at 260° C. to initiate reaction. The reactor interior temperature was gradually raised until the reactor interior temperature reached 290° C. The time taken until the temperature of 290° C. was reached was 2 hours. Reaction was continued at the interior temperature of 290° C. The reaction was terminated when the conversion of the metallic silicon powder exceeded 20% of the metallic silicon powder charge. The results are shown in Table 1.

TABLE 1

|  | E 1 | CE 1 | CE 2 |
|---|---|---|---|
| Running time (hr) | 6 | 8 | 8 |
| Si consumption (%) | 24.6 | 22.6 | 23.2 |
| STY (g/kg·hr) | 188 | 129 | 133 |
| MeHSiCl$_2$ (wt %) | 1.8 | 4.7 | 4.3 |
| Me$_3$SiCl (wt %) | 2.6 | 2 | 2.2 |
| MeSiCl$_3$ (wt %) | 7.1 | 8.3 | 8.1 |
| Me$_2$SiCl$_2$ (wt %) | 86 | 81.9 | 81.3 |
| R (wt %) | 2.5 | 3.1 | 4.1 |

A comparison of Example 1 with Comparative Example 1 reveals that Example 1 wherein the metallic silicon powder is preheated at a temperature above 20° C. before the catalyst is added brings the consumption of metallic silicon powder above 20% within a shorter time and yields a significantly favorable silane composition. As compared with Example 1, Comparative Example 2 wherein the catalyst is added after the metallic silicon powder is preheated, but to an insufficient extent, is low in STY and dimethyldichlorosilane proportion.

The present invention is successful in preventing the copper catalyst from being sintered by thermal hysteresis and activating a catalysis on the contact mass so that a high catalytic activity ensures a high selectivity at the start of reaction. The desired dialkyldihalosilane can be produced at a high selectivity.

Japanese Patent Application No. 137655/1997 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A method for preparing a contact mass for use in the production of alkylhalosilanes, comprising:

fluidizing a metallic silicon powder with an inert gas, preheating the silicon powder at a temperature of 200° C. to 300° C. for about 1 to 15 hours while keeping the silicon powder fluidized, and after the preheating, adding a copper catalyst to the preheated silicon powder.

2. A method for producing alkylhalosilanes of the formula:

$$R_nSiX_{4-n}$$

wherein R is a lower alkyl group having 1 to 4 carbon atoms,

X is a halogen atom, and letter n is an integer of 0 to 3, which comprises:

fluidizing a metallic silicon powder with an inert gas, preheating the silicon powder at a temperature of 200° C. to 300° C. for about 1 to 15 hours while keeping the silicon powder fluidized, after the preheating, adding a copper catalyst to the preheated silicon powder to form a contact mass, and contacting a reactant gas containing an alkyl halide with the contact mass whereby the alkylhalosilanes are formed by direct synthesis.

3. The method of claim 1, wherein the metallic silicon powder has a particle size of 5 to 150 μm.

4. The method of claim 2, wherein the metallic silicon powder has a particle size of 5 to 150 μm.

5. The method of claim 1, wherein the copper catalyst is elemental copper, a copper alloy or a copper compound.

6. The method of claim 2, wherein the copper catalyst is elemental copper, a copper alloy or a copper compound.

7. The method of claim 1, wherein copper catalyst is loaded in an amount of 0.1 to 10 parts by weight per 100 parts by weight of the metallic silicon powder.

8. The method of claim 2, wherein copper catalyst is loaded in an amount of 0.1 to 10 parts by weight per 100 parts by weight of the metallic silicon powder.

9. The method of claim 1, wherein a metallic zinc, antimony or tin powder promoter is used with the copper catalyst.

10. The method of claim 2, wherein a metallic zinc, antimony or tin powder promoter is used with the copper catalyst.

11. The method of claim 2, wherein the alkyl halide is methyl chloride and the alkylhalosilanes produced include dimethyldichlorosilane.

12. The method of claim 1, wherein the preheating is conducted at a temperature of from 240° C. to 280° C.

13. The method of claim 2, wherein the preheating is conducted at a temperature of from 240° C. to 280° C.

14. The method of claim 1, wherein the preheating is conducted for 2 to 10 hours.

15. The method of claim 2, wherein the preheating is conducted for 2 to 10 hours.

16. The method of claim 2, wherein the direct synthesis reaction takes place at 250° C. to 350° C.

17. The method of claim 2, wherein the direct synthesis reaction takes place at 280° C. to 300° C.

* * * * *